United States Patent [19]

Mora

[11] 4,020,074

[45] Apr. 26, 1977

[54] NITROLAMINES

[75] Inventor: Camillo Corvi Mora, Milan, Italy

[73] Assignee: Camillo Corvi S.p.A., Piacenza, Italy

[22] Filed: Sept. 8, 1975

[21] Appl. No.: 611,333

Related U.S. Application Data

[62] Division of Ser. No. 378,008, July 10, 1973, abandoned.

[30] Foreign Application Priority Data

July 14, 1972 Italy .................................. 27021/72

[52] U.S. Cl. ...................... 260/293.58; 260/347.7; 424/267; 424/285

[51] Int. Cl.$^2$ ...................................... C07D 405/04

[58] Field of Search .................... 260/293.58, 347.7

[56] References Cited

UNITED STATES PATENTS

| | | | |
|---|---|---|---|
| 3,385,867 | 5/1968 | Chang | 424/285 |
| 3,494,938 | 2/1970 | Weil et al. | 424/285 |
| 3,567,833 | 3/1971 | Weil et al. | 424/285 |

*Primary Examiner*—G. Thomas Todd
*Attorney, Agent, or Firm*—Young & Thompson

[57] ABSTRACT

A process for the industrial production of terpene nitrolaminic derivatives, comprising a first step wherein the terpene nitroso-chlorides are prepared reacting in a concentrated organic acid medium, selected from formic acid or acetic acid, terpenic materials, selected from alpha-pinene, limonene, alpha-terpineol and the like, with concentrated hydrochloric acid, in the presence of compounds having the formula R—OH, wherein R is an alkyl group, having 1 to 7 carbon atoms, and of alkali nitrites; and a second step wherein the nitroso-chlorides, thus precipitated, are reacted after purification and recrystallization, with an aminic derivative, selected from ammonia, amines, amino-alcohols and amino-acids, in an organic solvent medium in a ratio of nitroso-chloride to aminic derivative of 1 : 1, at a temperature ranging between 50° and 70° C, for 2-6 hours; the so developed hydrochloric acid is neutralized by addition of an organic buffer salt or a tertiary amine; and finally the so obtained nitrolamine bases are purified by recrystallization from organic solvents.

2 Claims, No Drawings

NITROLAMINES

This is a division of application Ser. No. 378,008, filed July 10, 1973, now abandoned.

This invention relates to a process for industrial production of terpene nitrolamine derivatives and the products thereby obtained.

Accordingly, it is the primary object of the present invention to provide a process for industrial production of terpene nitrolamine derivatives.

The present invention also relates to the terpene nitro lamine derivatives thereby obtained.

The industrial process consists of a first step of preparing terpene nitroso-chlorides, and a second step of converting such terpene nitroso-chlorides to terpene nitrol-amines, and namely: in the first step, the terpene material is reacted in a concentrated organic acid such as formic acid of acetic acid medium, by adding concentrated HCl, in the presence of an excess amount with respect to the stoichiometric amount, of compounds having the formula R—OH, where R is alkyl (having 1 to 7 carbon atoms), and alkali nitrites (sodium, potassium nitrites), or in the presence of an excess amount with respect to the stoichiometric amount of alkali nitrites.

Under such conditions, the nitroso-chlorides precipitate from the reaction medium and are purified by washing with hydrosoluble organic solvents (such as methanol, ethanol) and recrystalized therefrom. Generally, such products are heat stable and of high purity (titer 95–98%). The yields, varying in dependance on the type of nitroso-chloride, would often exceed 90% of the theoretical amount.

In the second step of the process, the nitroso-chlorides so obtained are reacted with an amine derivative from those hereinafter specified, in an organic medium, such as methanol, ethanol, or other aliphatic alcohols, or ketones, such as acetone, methylethylketone and the like. The reaction temperatures are ranging between 50° and 70° C and the reaction times between 2 and 6 hours.

The hydrochloric acid, developed in the reaction, is neutralized by adding the reacting mass an organic buffer salt, such as sodium or potassium acetate, citrate or tartrate, or tertiary amines, which are effective by subtracting HCl, and not as substituents, when the reaction ratio of the nitroso-chloride and the substituent amine derivative is 1 : 1; or as a neutralizing agent, a double molar amount can be added of the substituent amine preselected for the reaction, whereby the excess forms the relative hydrosoluble hydrochloride, which can be readily removed by washing the nitrolamine base with water.

The nitrolaminic bases obtained are purified by recrystallization from organic solvents, or by distillation where oleous materials are involved.

Following purification, the nitrolaminic bases are dissolved in an anhydrous organic solvent, such as ethyl ether, ethyl acetate, and are treated with gaseous HCl so as to obtain the respective chlorhydrates; the latter generally crystallize from the solvent and may not require any further purification.

As raw terpene materials for the first step of the process according to the present invention, the terpene materials which can be converted to nitroso-chlorides according to the above process, namely such materials as: alphapinene, limonene, pinol, alphaterpineol are suitable; sylvestrene, carene, xanthene, beta-terpineol and terpinene could also be used.

Therefrom the nitroso-chlorides are obtained as shown in Table 1, wherein the respective melting points are indicated.

TABLE 1

| Nitrous-chlorides | Melting Point |
|---|---|
| Alpha-pinene nitroso-chloride | 110° C |
| D-limonene n troso-chloride | 103° – 104° C |
| Pinol nitroso-chloride | 118° C |
| D,L-alpha-terpineol nitroso-chloride | 120° – 122° C |
| Beta-terpinel nitroso-chloride | 102° – 103° C |
| Silvestrene nitroso-chloride | 106° – 107° C |
| Δ 3 carene nitroso-chloride | 101° – 102° C |
| Xanthene nitroso-chloride | 109° – 110° C |

From the nitroso-chlorides, the nitrolaminic simple and substituted derivatives thereof, are obtained in the second step, which nitrolaminic derivative is identified by the following characteristic grouping:

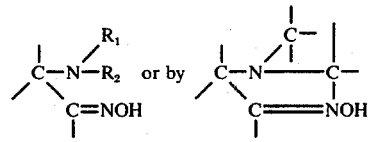

wherein $R_1$ and $R_2$ may both be H, or both radicals other than H, or wherein $R_1$ may be H and $R_2$ a radical other than H.

The above groupings will alternately occur according to whether the nitroso-chloride is reacted with ammonia, a primary amine compound R-$NH_2$, or a secondary amine compound

The amines apt to react with the nitroso-chlorides, produced according to the industrial process of the present invention, are: ammonia, primary or secondary aliphatic amines, aromatic amines, heterocyclic amines, such as piperidine, morpholine, piperazine, pyrrolidine, primary and secondary aliphatic di-amines.

Nitrolamine derivatives can be obtained by reacting a nitroso-chloride with amino-acids or amino-alcohols.

For a fuller understanding of the foregoing, hereinafter some examples will be given for mere illustrating and not limiting purposes.

A. PREPARATION OF NITROSO-CHLORIDES

EXAMPLE 1 — Alpha-pinene nitroso-chloride a. Laboratory preparation — 136 g alpha-pinene (95% purity) are converted to the nitroso-chloride by dissolving it in 300 ml of glacial acetic acid, in the presence of 150 ml of amyl nitrite, by addition of 50 ml 27% HCl mixted with 100 ml of acetic acid. The temperature is maintained in a range of 0°–5° C. The mixture is then cooled to −2° C and the nitroso-chloride is allowed to precipitate in a crystalline form. The product is filtered, washed with 50% methanol, and recrystallized from hot methanol. 180 — of nitroso-chloride are obtained, that is 90% of the theoretical, having m.p. 110° C.

b. Industrial preparation — 28 Kg of 95% alpha-pinene are dissolved in 60 l of glacial acetic acid; after cautiously cooling to 0° C in about 2 hours 15 Kg of sodium nitrite are added in a solution of a minimum amount of water, avoiding the development of nitroso-vapours; then 30 Kg of concentrated HCl dissolved in 60 l of acetic acid are slowly added maintaining an internal temperature of 0°–5° C.

The nitroso-chloride obtained has a titer of 99% the yield is 95% of the theoretical.

EXAMPLE 2 — Limonene nitroso-chloride a. Laboratory preparation — 136 g limonene are processed as in Example 1. 165 g of limonene nitroso-chloride are obtained, m.p. 103°–104° C.

b. Industrial preparation — 28 Kg of p-limonene are dissolved in 60 l of glacial acetic acid. The process is carried out as in Example 6.

The nitroso-chloride obtained has a 98% of titer, and the yield is 90% of the theoretical.

EXAMPLE 3 — Pinol nitroso-chloride a. Laboratory preparation — 152 g of pinol (95–98% purity) are converted to the nitroso-chloride after solution in 300 ml of glacial acetic acid and, bubbling treatment with 75 g methyl nitrite, by adding 50 ml 27% HCl, brought to 100 ml with concentrated acetic acid.

The process is carried out as in Example 1, obtaining 185 g of nitroso-chloride, that is a yield which is 85% of theoretical; m.p. 118° C.

b. Industrial preparation — 31 Kg of pinol, having a titer higher than 98%, are dropwise added to 60 l of glacial acetic acid in a 200 l glass reactor.

28 l of 1-pentanol are fed from a suitable charge vessel; 18 kg of $KNO_2$ are then added while cooling, so as not to exceed 2° C, in order to avoid any development of nitroso-vapours; afterwards, 30 Kg of concentrated HCl dissolved in 60 l of glacial acetic acid are dropwise added at the same temperature; the mass is then cooled to 0° C and diluted with 30 l of cold water; the separated nitroso-chloride is filtered by means of an anti-acid centrifuge: the obtained product is purified by crystallization from 50% ethanol.

38 Kg of product are obtained: m.p. 118° C.

The yield is higher than 98% of the theoretical value.

EXAMPLE 4 — Alpha-terpineol nitroso-chloride a. Laboratory preparation — 154 g of alpha-terpineol, dissolved in 300 ml of glacial acetic acid are converted to the corresponding nitroso-chloride by the same process described in Example 3. 208 g of nitroso-chloride are obtained, i.e. 95% of the theoretical value.

Nitroso-chloride titer: 97%; m.p. 120° C.

b. Industrial preparation — 32 Kg of alpha-terpineol, having a minimum titer of 98%, are dissolved in 50 l of 90% formic acid.

The reaction is carried out as in Example 1 with 15 Kg of sodium nitrite dissolved in a minimum amount of water and 30 Kg of concentrated HCl dissolved in 50 l of 90% formic acid.

39.5 Kg of nitroso-chloride having a titer of 98% are obtained with a yield of about 95% of the theoretical value.

B. PREPARATION OF NITROLAMINES

The nitroso-chlorides, produced according to the above examples, are treated with the amino-derivatives and the corresponding nitrolamines are obtained.

Hereinafter, the general procedure for preparing the nitrolamines derived from the reaction of the nitroso-chlorides with ammonia, as well as some particular examples relating to terpene nitro-amino-derivatives showing an outstanding activity as choleretic drugs are separated.

EXAMPLE 5 — Pinol-nitrolamine hydrochloride a. Laboratory preparation — 218 g of pinol nitroso-chloride are dissolved in 2,500 ml of 50% ethanol at a temperature of 70° C. 150 ml of 27% ammonia, diluted with 75 ml of ethanol, are added. Pinol nitrolamine is immediately formed.

After addition of diluted KOH, the mixture is filtered so that the formed inorganic salts are separated. The alcohol is evaporated under vacuum and an oleous residue of base nitrolamine is obtained, which is rectified under high vacuum (145° C at 20 mm). The oil obtained crystallizes in a solid product having a m.p. 83° C. 158 g base nitrolamine, having a titer of 99%, are obtained with 80% yield on the theoretical value.

The base can be converted to the corresponding chlorhydrate by dissolving 1 part by weight in 5 parts by volume of ethyl other and saturating with gaseous HCl. The precipitates of pinol-nitrolamine hydrosochloride is filtered and can be purified by recrystallization from water. The product obtained has a titer of 98%; m.p. 275° C.

b. Industrial preparation — 43.6 Kg of pinol nitroso-chloride are dissolved in a proper stainless steel reactor provided with a stirrer, cooling jacket and reflux cooler, in 500 l 50% ethanol at a temperature of 70° C. 20 Kg of 20% ammonia solution in ethanol are added. Upon reaction completion, the mixture is treated with 10.5 Kg of 50% KOH and filtered from the inorganic salts. The process is terminated as in Example 6.

The process yield is about 75% of the theoretical value.

EXAMPLE 6 — Pinol nitrol diethylamine hydrochloride a. Laboratory preparation — 218 g of pinol nitroso-chloride are treated in ethanol medium, as in Example 5, with 150 g of diethylamine. The precipitated substituted base nitrolamine is filtered and converted to the corresponding hydrochloride.

The product has a solubility in water of about 15% and m.p. 163° C. The product titer is 99% and the yield is 40% about of the theoretical value.

b. Industrial preparation — 43.5 Kg of pinol nitroso-chloride are dissolved in 250 l of ethanol at boiling temperature; 30 Kg of diethylamine are added. It is allowed to reflux boiling for 7 hours.

The solution, which is initially of a blue colour, slowly decolours to a light yellow colour.

The alcoholic solution is directly evaporated in the reactor by means of the vacuum of the liquid ring pump.

The obtained residue is dissolved in ethanol and converted to the corresponding hydrochloride, which is recrystallized from ethanol.

29 Kg of 99% product are obtained with a yield of 50% on the theoretical value.

The product so obtained corresponds to the following formula:

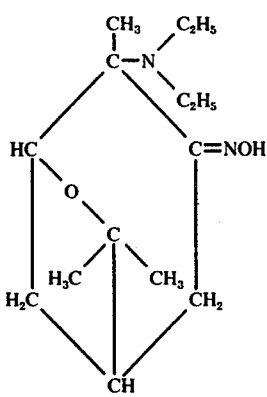

EXAMPLE 7 — Pinol nitrolpiperidine

Industrial preparation — 43.4 Kg of pinol nitrosochloride are dissolved in 300 l of ethanol at boiling temperature. 18 Kg of piperidine are then added. The solution is allowed to reflux boil for 6 hours. Ethanol is removed by vacuum evaporation and the preparation is completed as in Example 6. 30 Kg of 98% product are obtained; m.p. 207° C. The yield is about 50% of the theoretical value.

The product so obtained corresponds to the following formula:

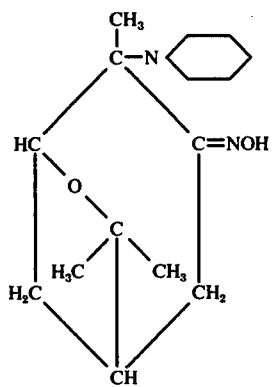

Toxicological properties

The products of Example 6 and Example 7 are of a very low toxicity. Oral administration to the Swiss rat has given for the product cited in Example 6 a $DL_{50}$ of 700 mg/kg, and for the product cited in Example 7 a $DL_{50}$ of 900 mg/kg; while in the Wistar rat the same was not calculable because up to a dose of 1000 mg/Kg, no mortalities occurred.

Pharmacological properties

The compounds of Example 6 and Example 7 are characterized by a higher choleretic activity and greater durability than conventional choleretic products (such as dehydrocholic acid). The pharmacological action has been studied on the previously anaesthetized Wistar rat, the percentage increase in the base choleresis after administration of the products being studied.

Wistar rats are used, as fasted 16 hours prior to test and divided into groups of 15 animals each.

After anaesthesia with urethane at a dose of 1 g/Kg, endoperitoneally, and after explorative laparotomy, the choledocus is catheterized by a thin polyethylene cannula, the free end of which goes into a 10 ml test tube graduated in tenths.

The choleresis is checked every 30 minutes during a standard observation period of 1 hour, then the products being tested are administered in the amount of one dose for each group of 15 rats, and 2 or 3 doses per product.

Then, every 30 minutes the amount of bile secreted during the first 2 hours is measured.

For each group of 15 animals under treatment, the increase and decrease percentage in the average cholereasis is established.

In the following table, the obtained results are shown as related to dehydrocholic acid:

| Material | Dose mg/Kg | % Volume of the biliar flow, 1h | After 2h |
| --- | --- | --- | --- |
| Dehydrocholic acid | 100 subcutaneous | +25 | +70 |
|  | 50 | +25 | +24 |
|  | 25 | +14 | +22 |
|  | 200 os | +34 | +36 |
| Product of Example 6 | 100 sub cutaneous | +52 | +75 |
|  | 50 | +48 | +53 |
|  | 25 | +10 | +33 |
|  | 200 os | +44 | +43 |
| Product of Example 7 | 100 sub cutaneous | +39 | +79 |

What is claimed is:

1. A nitrolamine selected from the group consisting of a compound of the formula

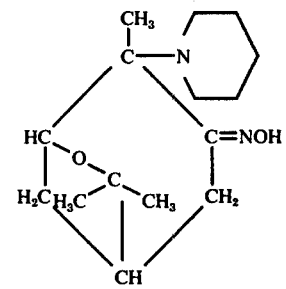

and the hydrochloride thereof.

2. A nitrolamine selected from the group consisting of a compound of the formula

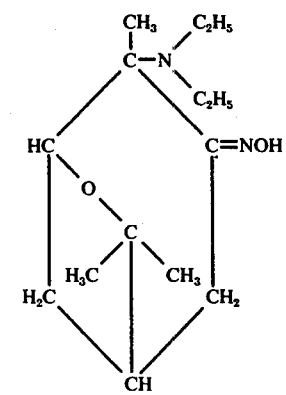

and the hydrochloride thereof.

* * * * *